(12) United States Patent
Haubrich et al.

(10) Patent No.: US 8,065,018 B2
(45) Date of Patent: Nov. 22, 2011

(54) SYSTEM AND METHOD FOR UNSCHEDULED WIRELESS COMMUNICATION WITH A MEDICAL DEVICE

(75) Inventors: Gregory J. Haubrich, Champlin, MN (US); Len D. Twetan, Excelsior, MN (US); David Peichel, Minneapolis, MN (US); Charles H. Dudding, Lino Lakes, MN (US); George C. Rosar, Minneapolis, MN (US); Quentin S. Denzene, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 358 days.

(21) Appl. No.: 11/224,593

(22) Filed: Sep. 12, 2005

(65) Prior Publication Data

US 2007/0060053 A1 Mar. 15, 2007

(51) Int. Cl.
*A61N 1/00* (2006.01)

(52) U.S. Cl. .................. 607/60; 607/30; 607/32

(58) Field of Classification Search ............ 607/30, 607/32, 60
See application file for complete search history.

(56) References Cited

U.S. PATENT DOCUMENTS

| | | | |
|---|---|---|---|
| 4,276,618 A | 6/1981 | Green | |
| 4,786,903 A | 11/1988 | Grindahl et al. | |
| 4,799,059 A * | 1/1989 | Grindahl et al. | 340/870.03 |
| 5,324,315 A | 6/1994 | Grevious | |
| 5,350,407 A | 9/1994 | McClure et al. | |
| 5,350,411 A | 9/1994 | Ryan et al. | |
| 5,549,113 A | 8/1996 | Halleck et al. | |
| 5,600,707 A | 2/1997 | Miller, II | |
| 5,752,977 A | 5/1998 | Grevious et al. | |
| 5,843,139 A * | 12/1998 | Goedeke et al. | 607/32 |
| 5,904,708 A | 5/1999 | Goedeke | |
| 5,995,874 A * | 11/1999 | Borza | 607/61 |
| 6,219,580 B1 * | 4/2001 | Faltys et al. | 607/57 |
| 6,223,083 B1 * | 4/2001 | Rosar | 607/60 |
| 6,335,953 B1 | 1/2002 | Sanderford, Jr. et al. | |

(Continued)

FOREIGN PATENT DOCUMENTS

EP 0717510 6/1996

(Continued)

OTHER PUBLICATIONS

International Search Report, PCT/US2006/035597, Jun. 3, 2007, 6 pages.

(Continued)

*Primary Examiner* — Niketa Patel
*Assistant Examiner* — Nicole F Lavert
(74) *Attorney, Agent, or Firm* — Stephen W. Bauer; Michael J. Ostrom

(57) ABSTRACT

Unscheduled wireless communication with a medical device is achieved by operating a receiver of the medical device in a series of modes. Each mode provides an increasingly selective evaluation of received RF energy. The receiver, when operating in a first mode, is capable of detecting the presence of RF energy transmitted from a communicating device. The receiver, when operating in a second mode, consumes more energy than the first mode and analyzes the RF energy to determine whether it contains the appropriate type of modulation. When operating in a third mode, the receiver consumes more energy than the second mode, and operates the full receiver to begin communication with the communicating device. The receiver opens a communication session after the RF energy has passed the evaluation by the series of modes to receive an unscheduled communication.

22 Claims, 5 Drawing Sheets

U.S. PATENT DOCUMENTS

| | | |
|---|---|---|
| 6,381,492 B1 * | 4/2002 | Rockwell et al. ............... 607/5 |
| 6,443,891 B1 | 9/2002 | Grevious |
| 6,631,296 B1 * | 10/2003 | Parramon et al. ............ 607/61 |
| 6,644,321 B1 | 11/2003 | Behm |
| 6,687,543 B1 | 2/2004 | Isaac et al. |
| 6,704,602 B2 | 3/2004 | Berg et al. |
| 6,738,670 B1 | 5/2004 | Almendinger et al. |
| 6,829,493 B1 | 12/2004 | Hunzinger |
| 6,897,788 B2 * | 5/2005 | Khair et al. ............ 340/870.16 |
| 6,993,393 B2 | 1/2006 | Von Arx et al. |
| 2001/0012955 A1 * | 8/2001 | Goedeke et al. ............ 607/27 |
| 2002/0026224 A1 | 2/2002 | Thompson et al. |
| 2002/0103514 A1 * | 8/2002 | Abrahamson .................. 607/60 |
| 2002/0123672 A1 * | 9/2002 | Christophersom et al. ... 600/300 |
| 2002/0143372 A1 * | 10/2002 | Snell et al. .................... 607/30 |
| 2002/0183806 A1 * | 12/2002 | Abrahamson et al. ......... 607/60 |
| 2003/0069614 A1 | 4/2003 | Bowman, IV et al. |
| 2003/0097157 A1 * | 5/2003 | Wohlgemuth et al. ......... 607/27 |
| 2003/0114898 A1 | 6/2003 | Von Arx et al. |
| 2003/0187484 A1 * | 10/2003 | Davis et al. .................... 607/60 |
| 2003/0229383 A1 | 12/2003 | Whitehurst et al. |
| 2004/0127959 A1 * | 7/2004 | Amundson et al. ............ 607/60 |
| 2004/0167587 A1 * | 8/2004 | Thompson .................... 607/60 |
| 2004/0172104 A1 | 9/2004 | Berg et al. |
| 2004/0176811 A1 * | 9/2004 | Von Arx et al. ................ 607/32 |
| 2004/0176822 A1 * | 9/2004 | Thompson et al. ............ 607/60 |
| 2005/0249236 A1 | 11/2005 | Walden |
| 2006/0097157 A1 | 5/2006 | Ouyang et al. |
| 2007/0049983 A1 * | 3/2007 | Freeberg ........................ 607/32 |
| 2007/0260293 A1 * | 11/2007 | Carpenter et al. ............. 607/60 |

FOREIGN PATENT DOCUMENTS

| | | |
|---|---|---|
| EP | 1264614 | 12/2002 |
| EP | 1495783 | 1/2005 |
| JP | 10256928 | 9/1998 |
| JP | 20042080704 | 7/2004 |
| WO | 9702510 | 7/1997 |
| WO | 0031998 | 6/2000 |
| WO | 0224064 | 3/2002 |
| WO | 03095024 | 11/2003 |

OTHER PUBLICATIONS

International Search Report, PCT/US2006/035598, Mar. 7, 2007, 5 pages.

* cited by examiner

SYSTEM AND METHOD FOR UNSCHEDULED WIRELESS COMMUNICATION WITH A MEDICAL DEVICE

CROSS-REFERENCE TO RELATED APPLICATION(S)

Reference is made to the following applications, filed concurrently herewith: U.S. patent application Ser. No. 11/224,591, now U.S. Pat. No. 7,890,191 issued Feb. 15, 2011, entitled "SYSTEM AND METHOD FOR UNSCHEDULED WIRELESS COMMUNICATION WITH A MEDICAL DEVICE," by Quentin S. Denzene and George C. Rosar: U.S. patent application Ser. No. 11/224,595, still pending, entitled "COMMUNICATION SYSTEM AND METHOD WITH PREAMBLE ENCODING FOR AN IMPLANTABLE MEDICAL DEVICE," by Gregory J. Haubrich, Javaid Masoud, George C. Rosar, Glenn Spital, and Quentin S. Denzene; and U.S. patent application Ser. No. 11/22,594, still pending, entitled "IMPLANTABLE MEDICAL DEVICE COMMUNICATION SYSTEM WITH MACRO AND MICRO SAMPLING INTERVALS," by Glen Spital, incorporated herein by reference in their entireties.

FIELD OF THE INVENTION

The present invention relates generally to implantable medical devices, and more particularly, to wireless communication with implantable medical devices.

BACKGROUND OF THE INVENTION

Current implantable medical devices (IMDs) provide countless therapies and monitor a wide variety of physiological events. With the increased uses of IMDs has also come the need for improved methods of communicating with and between IMDs.

Conventionally, communication with IMDs has been with magnetic field communication systems. Such systems, however, are generally only capable of communicating over very short distances, on the order of a few inches. As a result, a magnetic head of a programmer (or other external device) needs to be placed near to the IMD for communication to occur. More recently, radio frequency (RF) based communication systems have been developed for use with IMDs. RF communication provides a number of benefits over magnetic field communication systems, including much greater communication distances. However, conventional RF communication systems also consume more battery power than magnetic field communication systems.

DETAILED DESCRIPTION

The present invention includes a system and method for unscheduled, automatic wireless communication with a medical device. A medical device includes a receiver capable of being operated in a plurality of sequential modes. When operating in each consecutive mode, the receiver provides an increasingly selective evaluation of the RF energy. After passing the evaluation, the receiver receives the unscheduled communication.

Figure 1:
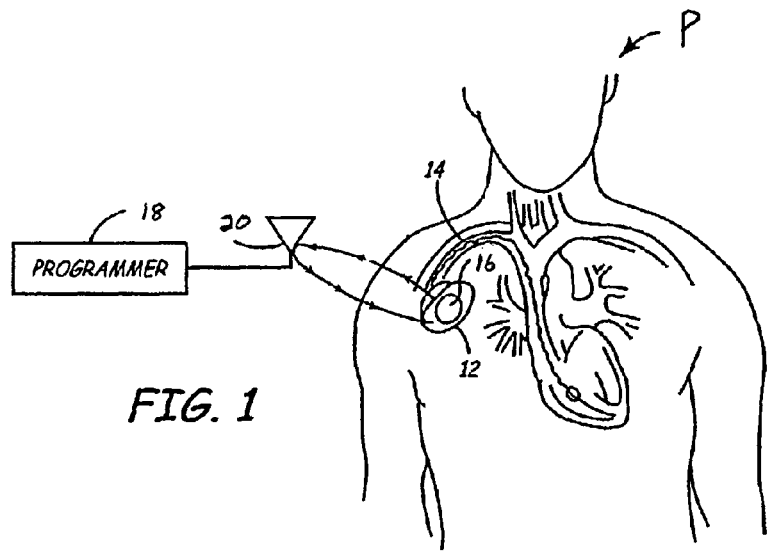
FIG. 1 is a schematic diagram illustrating bi-directional RF communication between an implantable medical device (IMD) and a programmer.

FIG. 1 is a schematic diagram illustrating bi-directional RF communication between IMD 12, which includes lead 14 and antenna 16. In one embodiment, IMD 12 is an implantable cardioverter defibrillator (ICD), but the present invention is equally applicable to many types of medical devices, including both implantable medical devices and external medical devices (XMD). IMD 12 is capable of providing therapies and/or sensing physiological events of the heart of patient P via lead 14. Antenna 16 is used to communicate with programmer 18 and may be any device capable of sending or receiving electromagnetic waves, including a surface mounted antenna, inductor, or half-wave strip.

Programmer 18 is an external programming unit capable of bi-directional communication with IMD 12 via antenna 20. In alternate embodiments, programmer 18 may be replaced by any device capable of communicating with IMD 12. Antenna 20 may be any type of RF antenna capable of communicating in the desired RF frequencies with IMD 12, and may be located inside or outside of a housing of programmer 18.

Figure 2:
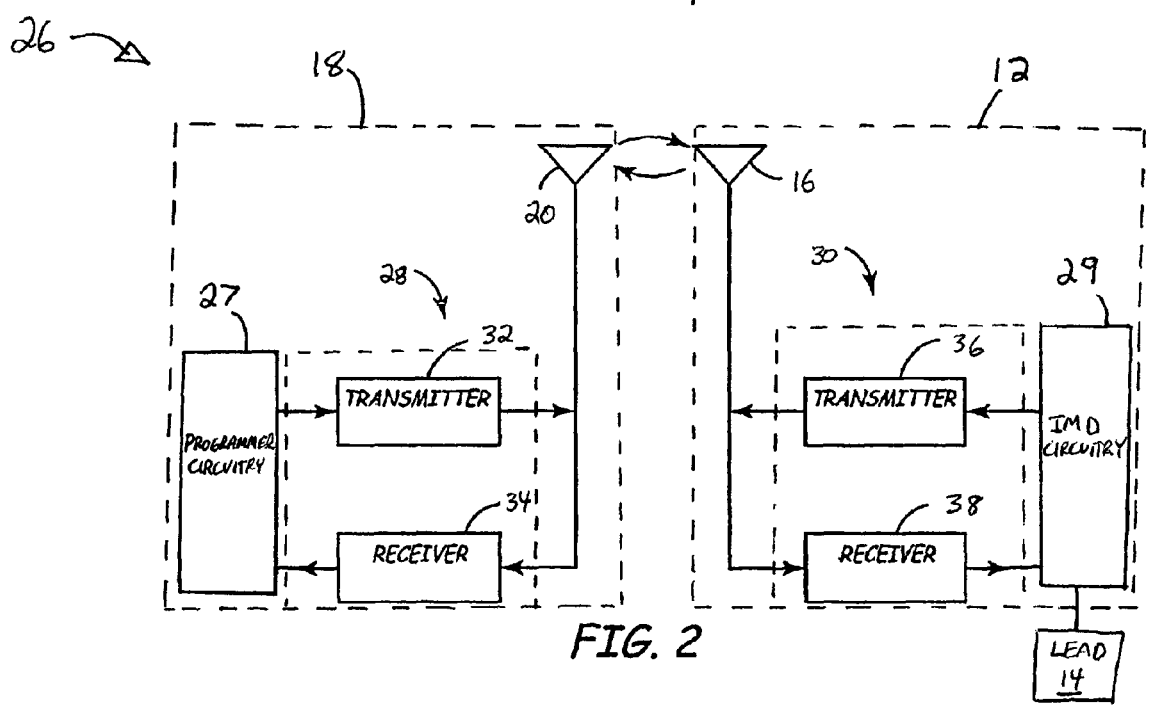
FIG. 2 is a block diagram illustrating the RF communication system components of the IMD and programmer.

FIG. 2 is a block diagram illustrating some of the functional components of IMD 12 and programmer 18 that make up RF communication system 26. Programmer 18 includes antenna 20, programmer circuitry 27, and transceiver 28. Antenna 20 is coupled to transceiver 28 of programmer 18. Programmer circuitry 27 includes a microcomputer and software to control the operation of programmer 18. Transceiver 28, coupled to antenna 20, enables programmer circuitry 27 to transmit and receive communications with IMD 12. Transceiver 28 of programmer 18 includes transmitter 32 and receiver 34.

IMD 12 includes antenna 16, IMD circuitry 29, and transceiver 30. IMD circuitry 29 includes a microprocessor, therapy delivery circuitry for delivering a therapy through lead 14, and sensors for detecting electrical signals on lead 14. Transceiver 30, coupled to antenna 16, enables IMD circuitry 29 to transmit and receive communications with programmer 18. Transceiver 30 includes transmitter 36 and receiver 38.

Because IMD 12 has a finite battery capacity, an important consideration in the design of RF communication system 26 is the energy efficiency of IMD 12. A substantial factor in the energy efficiency of IMD 12 is the time transceiver 30 spends either transmitting or receiving. Thus, any improvement in energy efficiency of transceiver 30 will lead to increased battery life of IMD 12. Energy efficiency is less of an issue in the design of programmer 18, because programmer 18 is generally connected to an external power source such as a 120V AC. Therefore, methods of operating transceivers 28 and 30 which reduce the energy consumption of transceiver 30, even in exchange for additional energy consumption of transceiver 28, are beneficial.

The ability to handle unscheduled communications between programmer 18 and IMD 12 is a desired feature of IMD 12. For example, a caregiver may want to use programmer 18 during an office visit to retrieve information from IMD 12. However, the capability to handle unscheduled communication has conventionally either required significant energy consumption by IMD 12 or user intervention.

The present invention provides a more energy efficient, automatic method of communicating with IMD 12. In particular, the IMD includes a receiver capable of operating in a plurality of modes, each having different levels of energy consumption. However, before describing the receiver in detail, the RF transmission by programmer 18 will be discussed.

Figure 3:
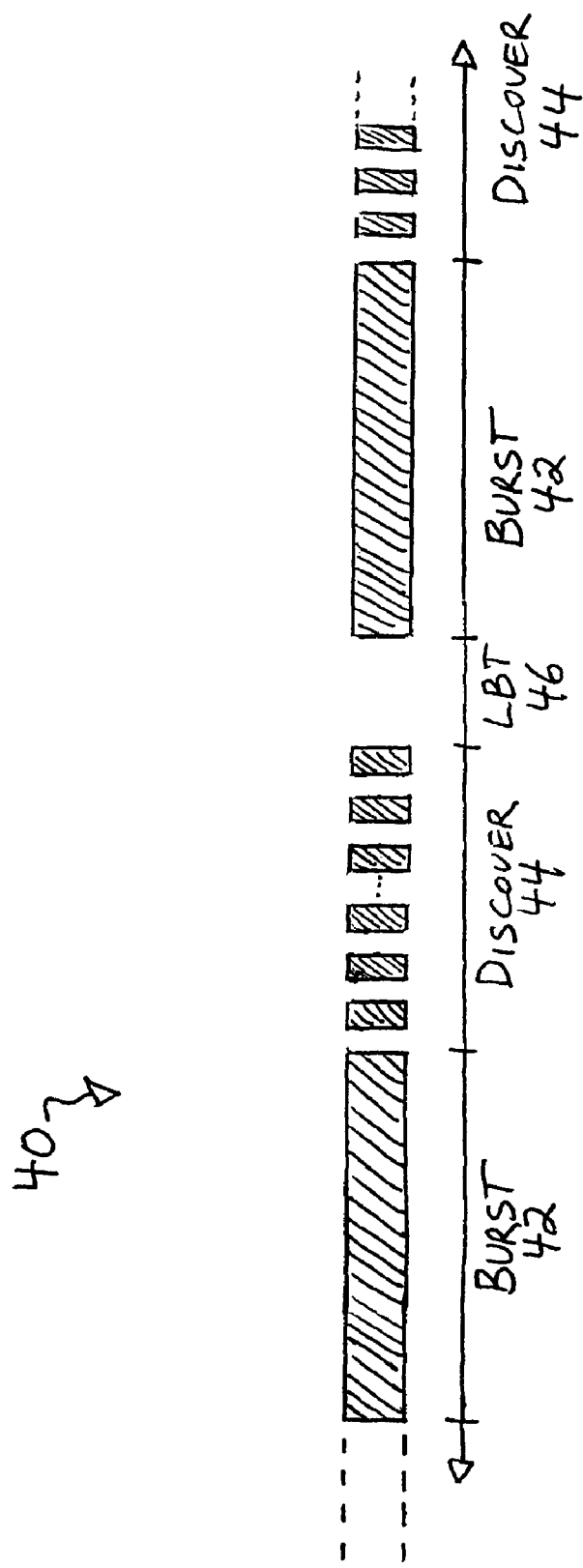
FIG. 3 is one embodiment of an RF transmission, transmitted by the programmer to initiate an unscheduled communication with the IMD.

FIG. 3 (not drawn to scale) is one embodiment of an RF transmission 40 that is transmitted by programmer 18 to initiate an unscheduled communication with IMD 12. Transmission 40 includes a repeating pattern having burst period 42, discover period 44, and Listen Before Talk (LBT) period 46.

In one embodiment, burst period 42 is a repetitive on-off-keyed (OOK) sequence equivalent to a series of alternating 0 and 1 bits where each bit transmission takes fifty microseconds, resulting in a 10 kHz pattern. In other embodiments, burst period 42 can be any repetitive pattern that can be detected by receiver 38 of IMD 12 to verify that a received transmission was transmitted by programmer 18. Burst period 42 generally lasts for a fixed period of time, such as 3 seconds.

Discover period 44 follows burst period 42 and is a period in which various transmissions by programmer 18 and IMD 12 take place according to a transmission protocol. As part of this protocol, transmissions by programmer 18 are followed by periods of listening, during which periods IMD 12 may transmit, if desired. In one embodiment, discover period 44 includes a period during which programmer 18 transmits for 20.1 milliseconds, followed by a period of listening for 15.0 milliseconds. Discover period 44 lasts for a fixed period of time, such as for 2 seconds. Following discover period 44 is LBT period 46, described below, which is a 0.7 second period during which no communication takes place.

Typically, IMDs communicate over the Medical Instrument Communication (MICs) band with frequencies ranging from about 402 to 405 MHz. This band-range is generally divided into ten channels spaced evenly within the band. Prior to transmission over the MICs band, the FCC currently requires that an external device must scan each of the ten channels and identify for broadcast the channel with the least amount of noise (referred to as the "least interference channel") or any channel below an FCC-specified RF level. This process must then be repeated at least every five seconds until a communication session is opened with a device. The period of time in which the external device scans the channels of the MICs band defines LBT period 46. Although the present invention is described with reference to communication over the MICs band, the invention is applicable to other communication bands. Alternatively, RF transmission 40 includes only a single LBT period 46, resulting in alternating burst and discover periods 42 and 44 for the remainder of RF transmission 40.

Figure 4:
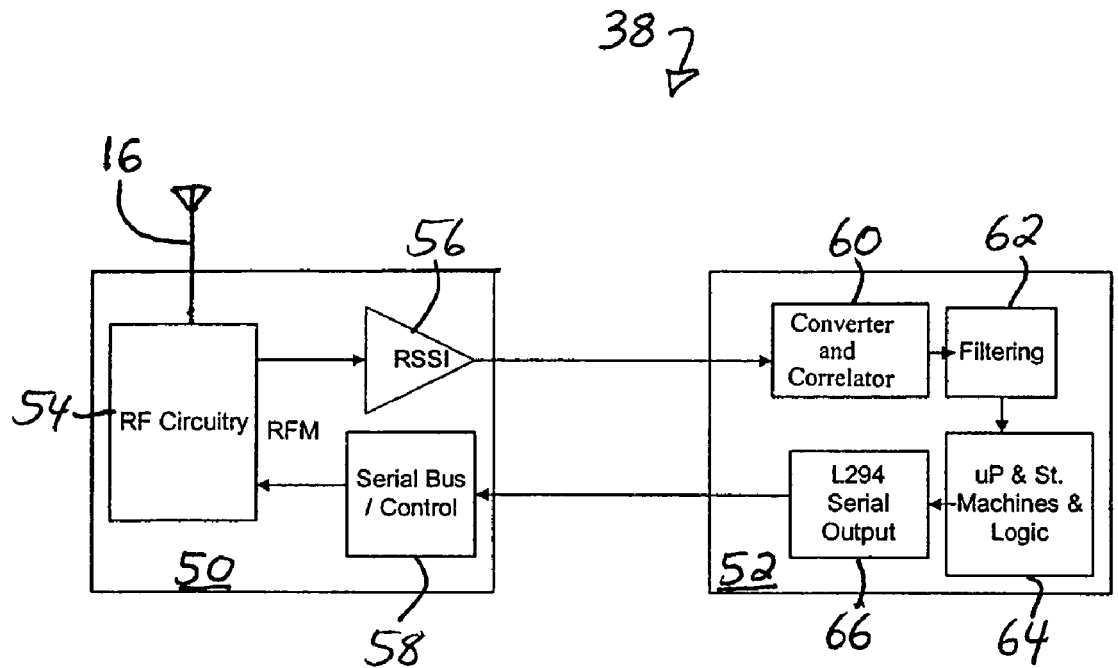
FIG. 4 is a block diagram of an antenna and a receiver of the IMD.

FIG. 4 is a block diagram receiver 38 of IMD 12 along with antenna 16 for reception of RF transmission 40 from programmer 18. Receiver 38 includes RF module 50 and telemetry digital hardware 52, which in one embodiment are separate integrated circuits. RF module 50 includes RF circuitry 54, Received Signal Strength Indicator (RSSI) 56, and serial bus/control 58.

RF circuitry 54 comprises one or more channels of receiver components such as voltage controlled oscillators (VCO), amplifiers, mixers, oscillators, and detectors that enable RF circuitry 54 to receive an RF signal from antenna 16, filter the signal, and remove the RF carrier frequency. RSSI 56 receives an output from RF circuitry 54 and provides an analog or digital output indicative of the strength of an RF signal received by antenna 16. Serial bus/control 58 provides control and serial communication capabilities to receiver 38. Serial bus/control 58 includes RAM buffers, control and status registers, and interrupt lines, as well as a synchronous bus and transmit and receive serial lines.

Telemetry digital hardware 52 includes converter/correlator 60, filter 62, microprocessor 64, and serial output 66. Converter/correlator 60 converts the output received from RSSI 56 to DC data (if an analog output) and determines how well correlated the received data is to an appropriate pattern. The output of converter/correlator 60 is filtered by filter 62 before it is sent to microprocessor 64. Microprocessor 64 includes a processor, state machines, logic, and random access memory (RAM) and functions as both the controller of receiver 38 and the interface between receiver 38 and other components of IMD 12. Microprocessor 64 receives the filtered output from filter 62. Serial output 66 operates to coordinate communications between RF module 50 and telemetry digital hardware 52. The interaction of these various elements of receiver 38 will be described further with reference to FIGS. 5 and 6.

Figure 5:
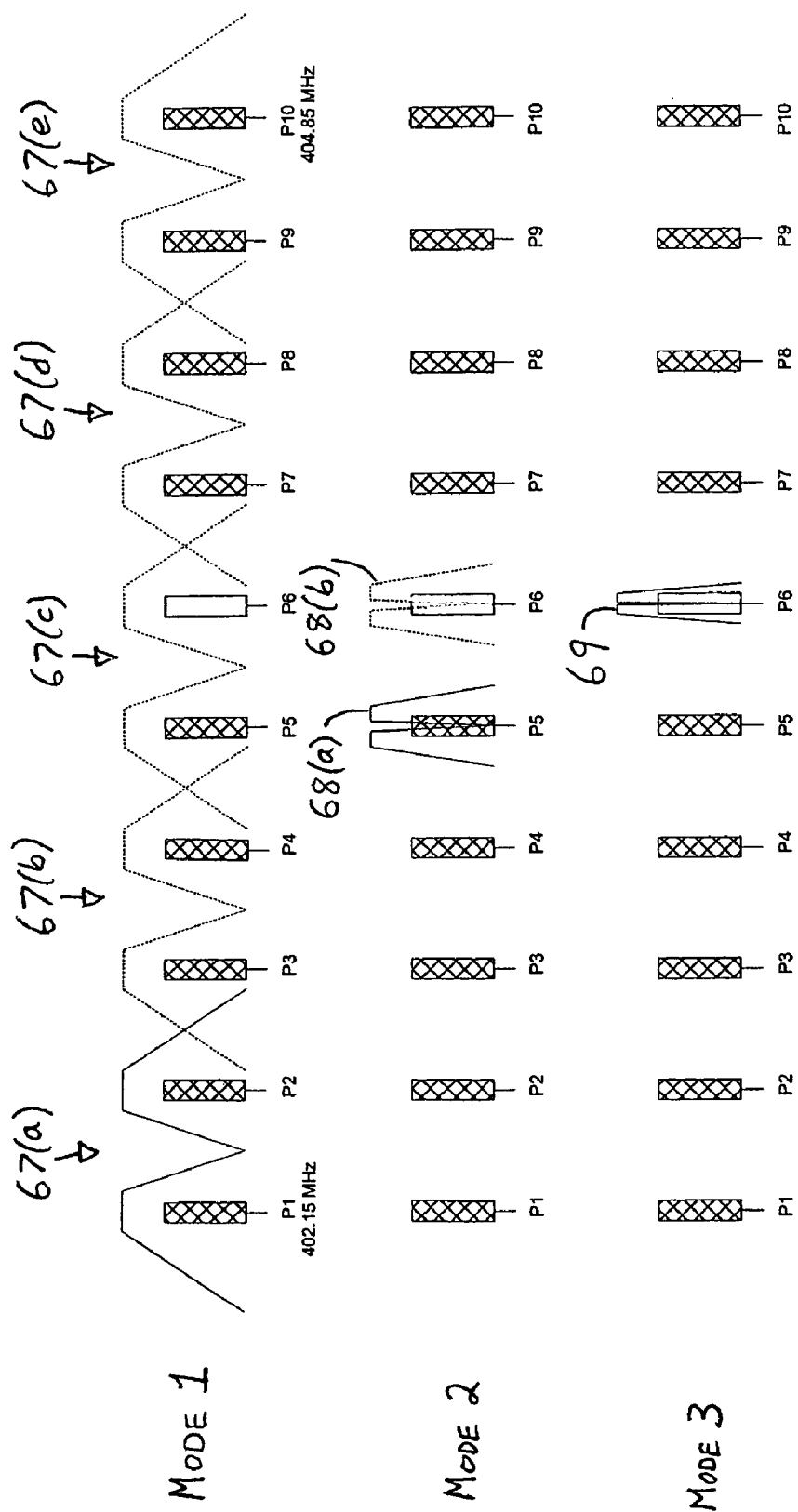
FIG. 5 is a spectral diagram illustrating three sequential receiver modes.

FIG. 5 is a spectral diagram of the MICs band from 402 MHz to 405 MHz, and illustrates the three receiver modes (Modes 1-3) of receiver 38. Within the MICs band are ten communication channels (P1-P10). The center frequency of each channel is spaced about 300 kHz from the center frequency of the next channel. For example, channel P1 is centered at 402.15 MHz, channel P2 is centered at 402.45 MHz, and channel P10 is centered at 404.85 MHz. As described above, FCC regulations require that programmer 18 broadcast on the least interference channel or any channel below the FCC minimum RF level. As a result, IMD 12 does not know prior to transmission which channel will be chosen by programmer 18. In the figure, communication channel P6, depicted by an open box, contains RF transmission 40, and channels P1-P5 and P7-P10, depicted by cross-hatched boxed, do not contain RF transmission 40.

The operation of receiver 38 depends on which of the three receiver modes it is currently operating in. When operating in Mode 1, receiver 38 operates in a wide bandwidth receiver mode that enables it to receive signals from two consecutive channels at once plus about 10 kHz. The bandwidth of the receiver is denoted by bandwidth 67. As shown in FIG. 5, the receiver operating in Mode 1 simultaneously samples two consecutive channels (such as P1 and P2 with bandwidth 67(a)). During each sample, receiver 38 checks for the presence of RF energy within those channels. Receiver 38 then proceeds through the five pairs of channels (67(b) through 67(e)) until each pair has been sampled. Because receiver 38 only performs a simple analysis of energy present, and because of the small sample time, receiver 38 operating in Mode 1 requires very low energy consumption. In this example, receiver 38 would detect the transmitted energy during sampling of channels P5 and P6, due to the presence of RF transmission 40 on channel P6.

Receiver 38 adjusts to the appropriate receiver frequencies by adjusting a VCO (not shown) of RF circuitry 54. In one embodiment, receiver 38 adjusts the VCO between five different voltages, each voltage approximately that needed to adjust receiver 38 to center on one of the five channel pairs. In another embodiment, the VCO is swept gradually through a voltage range encompassing the five voltages, such that receiver 38 passed through each of the five channel pairs. In another embodiment, receiver 38 adjusts the VCO between five different voltages, but then attempts to lock on to a received signal frequency, if any.

When RF energy is detected by receiver 38 in Mode 1, receiver 38 next adjusts itself to operate in Mode 2. In this mode, receiver 38 operates in a medium bandwidth receiver mode, represented by bandwidth 68, so that it receives RF energy of only those frequencies within a single channel plus about 30 kHz. In this example, where RF energy is initially detected on either channel P5 or P6, receiver 38 need only sample those channels. If energy is initially detected in more than one pair of channels, then additional samples may also be taken. In Mode 2, receiver 38 performs a more rigorous evaluation of any received energy. Receiver 38 samples both channels and determines in which channel energy is present, and also whether its modulation conforms to the expected type of modulation of RF transmission 40. This will be described in more detail with reference to FIG. 6. In the example of FIG. 5, energy is detected in channel P6, and is found to have the appropriate modulation.

After detecting that energy present on channel P6 contains the appropriate modulation, receiver 38 can be fairly confident that the energy is RF transmission 40 by programmer 18. As a result, receiver 38 enters Mode 3, a full or high power receiver mode in which receiver 38 is adjusted to receive energy from only a single channel, represented by bandwidth 69. Receiver 38 receives the signal and determines the content of the transmitted message. If appropriate, a communication session is then opened with programmer 18.

In an alternate embodiment, receiver 38 maintains statistical records indicating which channels are most often selected by programmer 18 for transmission and/or which channels most often result in a false detection. These records can then be used by receiver 38 to adjust the order of the channel scan in Mode 1 to improve the response time of receiver 38. In this embodiment, receiver 38 begins each Mode 1 channel scan with the pair of channels that are most often selected by programmer 18 for transmission. It proceeds through the channels in order from the channels with the highest probability of transmission to those with the lowest, and/or from the channels with the lowest probability of false detection to those with the highest. As soon as energy is detected, receiver 38 adjusts to Mode 2 to further evaluate the detected energy.

Figure 6:
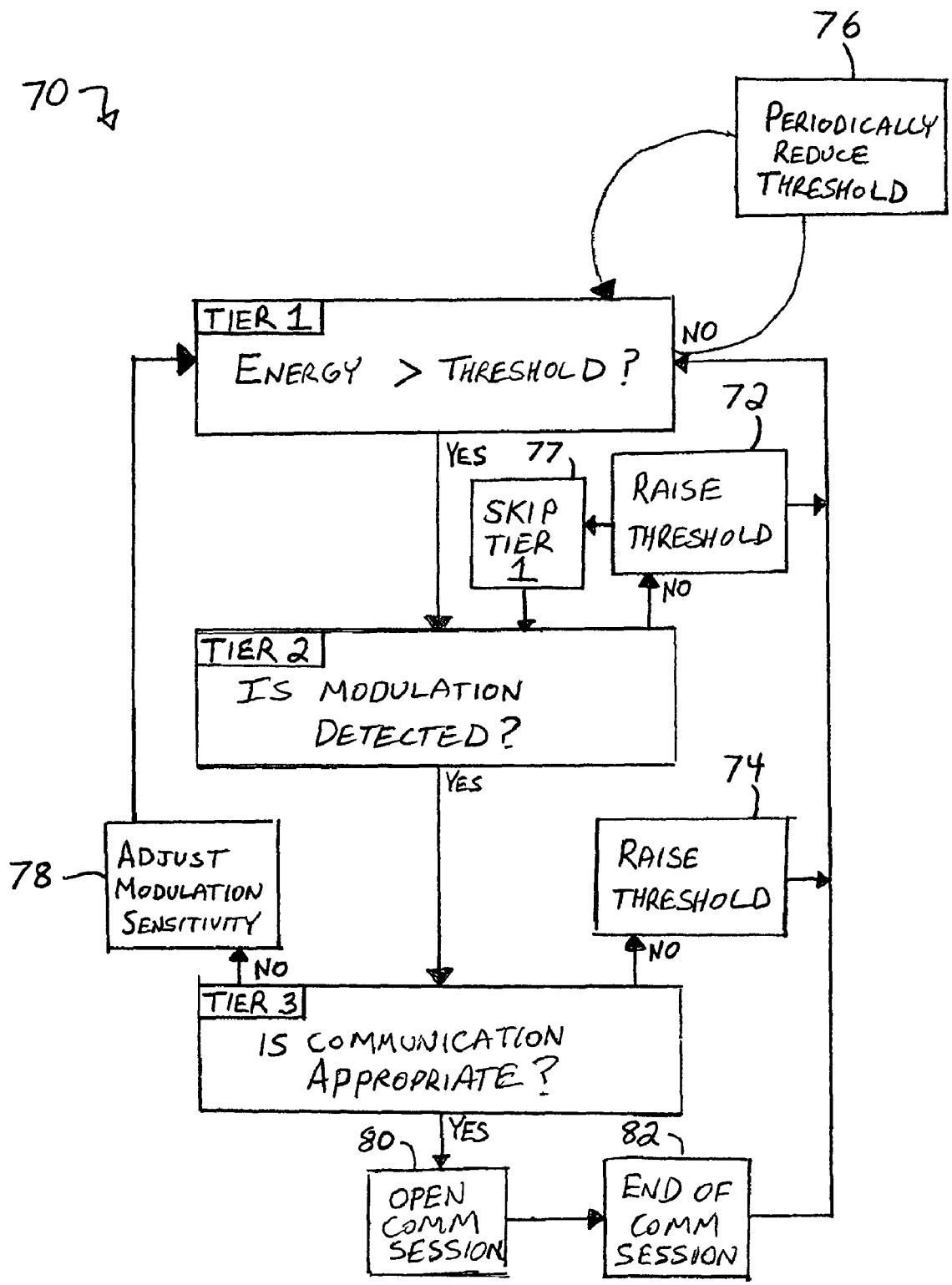
FIG. 6 is a flow diagram illustrating the multi-tiered method of operating receiver 38.

FIG. 6 is a flow diagram illustrating multi-tiered method 70 of operating receiver 38. This method is implemented in firmware and/or hardware of microprocessor 64 of receiver 38. In one embodiment of the invention, multi-tiered method 70 includes Tier 1, Tier 2, and Tier 3, where each tier corresponds to a mode of operating receiver 38. In addition, method 70 enables control over the number of false detections that occur, thereby reducing the energy consumed by the detection of undesired RF signals, by raising channel thresholds 72 and 74, periodically reducing thresholds 76, skipping Tier 1 operation 77, and adjusting modulation sensitivity 78. After receiver 38 has sequentially evaluated the RF energy with Tiers 1, 2, and 3, receiver 38 opens a communication session (step 80) with programmer 18. After the communication session is complete, receiver 38 ends the session (step 82), and returns to Tier 1 operation.

Multi-tiered method 70 begins at Tier 1 with receiver 38 in Mode 1, which is a very low power receiver mode that utilizes only a portion of receiver 38, including a mixer, and an intermediate frequency (IF) channel of RF circuitry 54 and RSSI 56. In one embodiment, the bandwidth of receiver 38 is set to receive two consecutive channels plus 10 kHz. Here, receiver 38 samples the energy on each pair of channels over a brief period of time (such as 150 microseconds) and determines whether a threshold level of energy is present in that pair of channels during the sample period. This is done by passing any received RF energy to RSSI 56, which then determines the strength of any received RF signal. Telemetry digital hardware 52 receives the strength indication from RSSI 56 and stores each RSSI value in RAM corresponding to the appropriate channel pairs. Telemetry digital hardware 52 also contains a threshold value stored in RAM locations for that channel pair that defines the minimum RSSI value that will trigger Tier 2 for each channel. After each pair of channels has been sampled, the RSSI values for the channel pair are compared to the corresponding threshold values by microprocessor 64. For any channel pair in which the RSSI value exceeds the threshold value, the energy on that channel is further scrutinized by entering Tier 2. Tier 2 and Tier 3 processing are only performed after any detected energy has passed Tier 1 scrutiny. In this way, significant energy savings can be realized because higher energy consuming receiver modes are not activated unless a potential RF transmission is present on a channel.

To conserve power when in Tier 1, receiver 38 is operated so that the total receiver on-time per channel pair is very brief (such as 150 microseconds). Because this receiver on-time is shorter than the listening periods of RF transmission 40 (during discover period 44 and LBT period 46), it is possible that receiver 38 could miss transmission 40 by turning on at a time when programmer 18 is not transmitting. The present invention solves this problem by repeating the scan of all pairs of channels after a fixed period to ensure that one of the channel samples will be taken during burst period 42 of RF transmission 40, if transmission 40 is being broadcast. There are many available sampling periods that can be selected that ensure that burst period 42 will be received, as illustrated in Table 1.

TABLE 1

| Nth Frame Sampling N = | Min. Sampling Period (sec) | Max. Sampling Period (sec) | Ave. Sampling Period (sec) |
| --- | --- | --- | --- |
| 1 | 2.7 | 3 | 2.85 |
| 2 | 8.4 | 8.7 | 8.55 |
| 3 | 14.1 | 14.4 | 14.25 |
| 4 | 19.8 | 20.1 | 19.95 |
| 5 | 25.5 | 25.8 | 25.65 |
| 6 | 31.2 | 31.5 | 31.35 |
| 7 | 36.9 | 37.2 | 37.05 |
| 8 | 42.6 | 42.9 | 42.75 |
| 9 | 48.3 | 48.6 | 48.45 |
| 10 | 54 | 54.3 | 54.15 |
| 11 | 59.7 | 60 | 59.85 |
| 12 | 65.4 | 65.7 | 65.55 |
| 13 | 71.1 | 71.4 | 71.25 |
| 14 | 76.8 | 77.1 | 76.95 |

Table 1 shows the first fourteen time periods during which a second channel sample could be taken to ensure that one of the two samples is taken during burst period 42, if present. Table 1 is based upon an embodiment in which burst period 42 is 3 seconds, discover period 44 is 2 seconds, and LBT period 46 is 0.7 seconds. In the table, N represents the number of frames (a frame is defined by one burst period 42, one discover period 44, and one LBT period 46) after the first sample. For example, for N=1, the second sample would take place one frame after the frame of the first sample, and for N=3, the second sample would take place three frames after the frame of the first sample. For each frame, Table 1 identifies a minimum sampling period, a maximum sampling period, and an average sampling period for this embodiment. The minimum sampling period is the minimum time needed between the first and the second sample to ensure that one of the samples will occur during burst period 42, if present. Similarly, the maximum sampling period is the maximum time needed between the first and the second sample to ensure that one of the samples will occur during burst period 42, if present. The average sampling period is the average of the minimum and the maximum sampling period, which will also ensure that one of the samples occurs during burst period 42, if present.

To further conserve energy consumption, the sampling periods may be varied based upon factors such as the time of day, patient P activity level, or any other measurable or detectable criteria. For example, IMD 12 may conserve energy during the night by increasing the time between samples, while increasing response time during the day by decreasing the time between samples. For example, if the day sampling period were 8.55 seconds, the night sampling period may be 19.95 seconds. Similarly, IMD 12 can also use activity sensors or other measurable or detectable criteria to dynamically adjust the sensing periods.

If any of the RSSI measurements obtained during the Tier 1 sampling periods exceeds the corresponding channel threshold values, receiver 38 enters Tier 2, as shown in FIG. 6. In Tier 2, receiver 38 is operated in Mode 2, which also utilizes only a portion of receiver 38, such as a mixer and an IF channel of RF circuitry 54, RSSI 56, and correlator 60, but takes a somewhat longer sample of the energy, thereby consuming more energy than Tier 1. In one embodiment, when operating in Mode 2, the bandwidth of receiver 38 is set to receive signals from a single channel plus 30 kHz. Any detected energy present on that channel is then evaluated to determine whether its detected modulation corresponds to an expected modulation of RF transmission 40.

Receiver 38 is centered on one of the two (or more) channels, for example channel P5. Receiver 38 takes a sample of the RF energy present on that channel for a period of time, such as 1.72 milliseconds. Because receiver 38 knows when burst period 42 was received in Tier 1, an appropriate period of time between that sample and the Tier 2 sample can be calculated based upon the time periods shown in Table 1. If the magnitude of the energy on this channel does not exceed the threshold value, then receiver 38 adjusts to the second channel and repeats the procedure.

When operating at Tier 2, receiver 38 not only determines on which channel the potential RF transmission is, but also evaluates the transmission for the appropriate modulation or pattern. To do so, receiver 38 provides the sample (for example 1.72 milliseconds) of the transmission, if any, to converter/correlator 60. Correlator 60 compares the data pattern in the sample to the appropriate data pattern for burst period 42 (such as a repetitive 0-1 pattern, or any other desired bit pattern). If correlator 60 determines that the data matches the appropriate pattern, the received RF energy is likely to be RF transmission 40 from programmer 18. As a result, receiver 38 initiates Tier 3 and powers up receiver Mode 3. If, however, correlator 60 determines that the received data (if any) is not correlated, and therefore is not RF transmission 40, receiver 38 returns to Tier 1 where it continues to periodically perform a channel scan.

In an alternate embodiment, receiver 38 samples for a variable period of time, rather than for a fixed period. Receiver 38, operating at Tier 2, begins evaluation of the data pattern contained in the potential RF transmission. If receiver 38 determines that the pattern is not appropriate, it returns to tier 1 operation. However, if the appropriate pattern is initially received, receiver 38 continues to evaluate the pattern until either the pattern diverges from the appropriate pattern or a predetermined period of time has passed. After such period of time, receiver 38 adjusts to receiver Mode 3 for further evaluation of the transmission.

Many other criteria could also be used to evaluate RF energy in Tier 2 of the present invention. For example, receiver 38 could detect AM or FM modulation, or any other recognizable characteristic of an RF transmission. In alternate embodiments, Tiers 1 and 2 may be combined into a single step, or one of Tiers 1 or 2 could be skipped entirely.

To maintain high sensitivity of receiver 38, it is desirable to allow a certain number of false signals to pass Tier 1 scrutiny. However, the more often receiver 38 is triggered to go beyond Tier 1, the more energy is consumed, which in turn reduces overall battery life. A balance between these conflicting goals is found through adaptive channel thresholds. Receiver 38 can periodically adjust the channel thresholds to maintain them just above the noise level or other interference present in each channel.

As previously described, receiver 38 stores threshold values in RAM for each channel pair that identify the minimum strength a signal must have (as measured by RSSI 56) before it will trigger receiver 38 to move into Tier 2. At some point, noise present in the channel may exceed the threshold value, which will result in a falsing that will trigger the transition to Tier 2, where receiver 38 will analyze the noise signal and determine that the noise does not have the appropriate modulation. As a result, receiver 38 will raise the threshold value (step 72) to a level greater than the noise signal received. However, to maintain the sensitivity of receiver 38, the channel threshold values are periodically decreased (step 76). The period of time in which the threshold values are decreased (step 76) depends on a desired falsing rate. A high falsing rate corresponds to greater battery consumption but increased sensitivity. A low falsing rate corresponds to lower battery consumption but decreased sensitivity. In one embodiment, receiver 38 has a 10% desired falsing rate for Tier 1 sensitivity, and receiver 38 will gradually adjust the threshold values to achieve this desired falsing rate.

Receiver 38 may also increase the thresholds after detecting that a false signal has caused receiver 38 to enter Tier 3 (step 74). In this way, receiver 38 can avoid repeatedly detecting and analyzing a signal already determined not to be RF transmission 40.

If noise causes receiver 38 to false at a rate higher than the desired falsing rate, FIG. 6 illustrates a provision for skipping Tier 1 evaluation (step 77) altogether for a period of time. In this scenario, channel scans would be performed by Tier 2, which would evaluate energy on each channel to determine whether it exceeds the threshold value and whether it is correlated with the appropriate modulation.

In an alternate embodiment, threshold values could be adjusted based upon a time averaged power consumption. In this embodiment, receiver 38 would keep track of an average power consumption over a period of time, such as hours, days, or months. Average power consumption could be estimated by receiver 38 by keeping track of the amount of time receiver 38 is ON. In this way, higher falsing rates could be permitted for a short period of time as long as the average power consumption was maintained within an acceptable amount. Furthermore, receiver 38 could then be controlled in such a way that it would not consume more than a specified maximum percentage of the battery power of IMD 12.

Once a received signal has passed both Tier 1 and Tier 2 scrutiny, that is, once the signal has the appropriate amplitude and modulation, it is highly likely that the signal is RF transmission 40. As a result, receiver 38 enters Tier 3 in which receiver 38 now operates in Mode 3. Receiver 38 is adjusted so that it receives signals from only a single channel bandwidth. In this mode receiver 38 draws more current and samples the energy for a longer period of time than in either of the previous modes, thereby consuming more energy. Once full receiver 38 has been powered up, it samples the received transmission to determine what message is being sent. If receiver 38 determines that communication is not appropriate, it raises the threshold value (step 74) for that channel and returns to Tier 1. Alternately, if receiver 38 determines that the transmission was not RF transmission 40, receiver 38 may also or alternatively adjust the modulation sensitivity of Tier 2 (step 78). For example, receiver 38 could adjust correlator 60 used in Tier 2 to require that a received signal be more highly correlated before it will be allowed to pass to Tier 3. After a period of time, receiver 38 would then return the modulation sensitivity to the original settings to achieve optimum sensitivity. In the same way that the Tier 1 falsing rate can be adjusted, Tier 2 can also be adjusted to conform to the desired modulation falsing rate, by adjusting the modulation sensitivity of Tier 2. In one embodiment, the Tier 2 modulation falsing rate is 5%, such that receiver 38 adjusts the modulation sensitivity up or down until 5% of all RF signals that trigger Tier 3 are determined to not be RF transmission 40.

Once Tier 3 evaluation is complete, such that receiver 38 determines that communication is appropriate, receiver 38 opens a communication session with programmer 18 (step 80). After the communication session is complete, receiver 38 ends the communication session (step 82). Receiver 38 then resumes Tier 1 operation.

Although the present invention has been described with reference to preferred embodiments, workers skilled in the art will recognize that changes may be made in form and detail without departing from the spirit and scope of the invention. Each tier of the multi-tiered method of operating receiver 38 could utilize a variety of detection schemes to determine when an external device is attempting to initiate RF communication with it. For example, receiver 38 at Tier 1 could sample or monitor for any type of signal, pattern, modulation, amplitude, or phase change. Furthermore, receiver 38 at Tier 1 could monitor for communications in other RF bands, or even non-RF communications such as an ultrasonic signal transmitted by a speaker in programmer 18 and received by a piezoelectric sensor coupled to receiver 38. Similarly, receiver 38 at Tiers 2 and 3 could also sample or monitor for any type of signal, pattern, modulation, amplitude, or phase change. The present invention is also not limited to a three-tiered method, but rather could be implemented with any number of receiver modes. The present invention has been described with reference to implantable medical devices and external units. It is recognized that in some situations it would be desirable to use the present invention for communication between implantable medical devices, between external units, among a wireless network of implantable or external devices, or to reverse the roles of the implantable medical device and the external unit.

What is claimed is:

1. A method for receiving an unscheduled communication by operating a receiver of a medical device over a communication band having a plurality of frequency-divided communication channels, said communication band divided into a plurality of bandwidths, each individual one of said plurality of bandwidths comprising a plurality of individual ones of said plurality of communication channels, comprising the steps of:
    operating said receiver in a first mode, comprising detecting radio frequency energy over a threshold sequentially over each individual one of said plurality of bandwidths;
    operating said receiver in a second mode if radio frequency energy over said threshold is detected, comprising identifying, in an individual one of said plurality of bandwidths in which said radio frequency energy over said threshold has been detected, an individual one of said plurality of communication channels having a radio frequency transmission; and
    opening a communication session to receive said radio frequency transmission on said individual one of said plurality of communication channels.

2. The method of claim 1, wherein the operating the receiver in a first mode step further comprises, evaluating a signal strength of the radio frequency energy.

3. The method of claim 2, wherein each individual one of the plurality of bandwidths comprises a pair of individual ones of said plurality of communication channels, and the operating the receiver in the first mode step further comprises:
    sampling the pair of individual ones of the plurality of communication channels of an individual one of the plurality of bandwidths for radio frequency energy;
    determining a first strength value representative of a relative strength of the radio frequency energy sampled in the sampling step;
    comparing the first strength value to a threshold value.

4. The method of claim 3, wherein the operating the receiver in the first mode step further comprises:
    waiting for a period of time based upon a frame length of the communication;
    sampling the pair of individual ones of the plurality of communication channels of the individual one of the plurality of bandwidths for the radio frequency energy after the period of time;
    determining a second strength value representative of a second strength of the radio frequency energy sampled in the sampling step;
    comparing the second strength value to the threshold value.

5. The method of claim 3, wherein the operating the receiver in a second mode step further comprises the step of evaluating a modulation of one of the communication channels of the pair of individual ones of the plurality of communication channels of the individual one of the plurality of bandwidths.

6. The method of claim 5, wherein the operating the receiver in a second mode step is only initiated if the first strength value exceeds the threshold value in the operating the receiver in the second mode step further comprises:
    sampling each individual one of the pairs of communication channels of the individual one of the plurality of bandwidths for radio frequency energy;
    determining a second value representative of a strength of the radio frequency energy in each individual one of the pairs of communication channels;
    comparing the second value to the threshold value for each of the pairs of communication channels;
    evaluating a modulation of radio frequency energy of any channel that exceeds the threshold value is correlated to a defined modulation.

7. The method of claim 6 further comprising increasing the threshold value if the modulation is not correlated to the defined modulation.

8. The method of claim 7, further comprising decreasing the threshold value after a threshold decrease period.

9. The method of claim 7, further comprising calculating the threshold decrease period to achieve a first falsing rate corresponding to a number of times an individual one of the pair of communication channels of the individual one of the plurality of bandwidths is erroneously determined to contain a radio frequency transmission.

10. The method of claim 5, further comprising the step of operating the receiver in a third mode, after the operating the receiver in a second mode step, comprising evaluating data contained within individual ones of the pair of communication channels of the individual one of the plurality of bandwidths determined in the operating the receiver in the second mode step to contain a radio frequency transmission.

11. The method of claim 10, wherein the operating the receiver in the third mode step further comprises evaluating a message contained within the radio frequency transmission to determine whether further communication is appropriate.

12. The method of claim 11, further comprising increasing the threshold value if further communication is not appropriate.

13. The method of claim 11, further comprising increasing a selectivity of the evaluating step if further communication is not appropriate.

14. The method of claim 13, further comprising decreasing the selectivity of the evaluating step after a modulation adjustment period.

15. The method of claim 14, further comprising calculating the modulation adjustment period to achieve a desired second falsing rate corresponding to a number of times an individual one of the pair of communication channels of the individual one of the plurality of bandwidths is erroneously determined to contain a radio frequency transmission.

16. A medical device that conducts radio frequency communication over a communication band comprising a plurality of frequency-divided communication channels, comprising:
 implantable medical device circuitry;
 a receiver operatively coupled to the implantable medical device circuitry and operating in a first mode and a second mode, the receiver detecting radio frequency energy over a first bandwidth when operating in the first mode and detecting radio frequency energy over a plurality of second bandwidths when operating in the second mode, the first bandwidth being narrower than the communication band and broader than the individual ones of the plurality of second bandwidths, the first bandwidth comprising a first subset of the plurality of communication channels;
 wherein, with the receiver operating in the first mode, the implantable medical device circuitry compares the radio frequency energy detected over the first bandwidth against a threshold;
 wherein the first bandwidth is shifted to incorporate a second subset of individual ones of the plurality of communication channels if the threshold exceeds the radio frequency energy, the second subset incorporating at least some different individual ones of the plurality of communication channels compared with the first subset;
 wherein the receiver switches from the first mode to the second mode if the radio frequency energy exceeds the threshold;
 wherein, after the receiver switches to the second mode, the implantable medical device circuitry identifies an individual one of the plurality of communication channels of the first bandwidth having a radio frequency transmission; and
 wherein the receiver receives data via the radio frequency transmission on the individual one of the plurality of communication channels of the first bandwidth having the radio frequency transmission.

17. The medical device of claim 16, wherein the first bandwidth comprises a pair of said plurality of communication channels.

18. The medical device of claim 17, the implantable medical device circuitry identifying, when the receiver is in the second mode, the individual one of the plurality of communication channels by sequentially correlating a modulation of the radio frequency energy over individual ones of the plurality of second bandwidths with a predetermined modulation.

19. The medical device of claim 18, wherein, if the modulation correlates with the predetermined modulation, the implantable medical device circuitry evaluates the radio frequency energy, and wherein, based on the evaluation, the receiver further operates in a third mode, the receiver detecting radio frequency energy over a third bandwidth when operating in the third mode, the third bandwidth being narrower than the individual ones of the plurality of second bandwidths and comprising one of the plurality of communication channels, the receiver receiving the data via the radio frequency transmission when operating in the third mode.

20. A medical device system for receiving data transmissions over a plurality of transmission channels, comprising:
 means for determining whether RF energy within pairs of transmission channels of the plurality of transmission channels exceed a first energy threshold;
 means for determining whether RF energy within each individual transmission channel of pairs of transmission channels determined to exceed the first energy threshold exceed a second energy threshold;
 means for determining whether a data pattern of a data transmission associated with an individual channel determined to exceed the second energy threshold matches a data pattern threshold and for identifying the individual transmission channel as containing a desired data transmission in response to the data pattern matching the data pattern threshold;
 means for verifying the identifying of the individual transmission channel as containing a desired data transmission; and
 means for opening a communication session to receive the desired data transmission on the individual transmission channel.

21. The system of claim 20, further comprising means for determining probabilities of transmission for each of the plurality of transmission channels and for adjusting an order of the determining, by the means for determining whether RF energy within pairs of transmission channels exceed the first energy threshold, in response to the determined probabilities.

22. The system of claim 20, further comprising means for determining, for each of the transmission channels, a probability of not being verified by the means for verifying when the transmission channels are identified as containing a desired data transmission, and for adjusting an order of the determining, by the means for determining whether RF energy within pairs of transmission channels exceed the first energy threshold, in response to the determined probabilities.

* * * * *